United States Patent
Keller et al.

(10) Patent No.: US 9,381,176 B2
(45) Date of Patent: Jul. 5, 2016

(54) E-PROSTANOID RECEPTOR, PTGER3, AS A NOVEL ANTI-DIABETIC THERAPEUTIC TARGET

(71) Applicant: Wisconsin Alumni Research Foundation, Madison, WI (US)

(72) Inventors: Mark Keller, McFarland, WI (US); Alan Attie, Madison, WI (US); Michelle Kimple, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 13/774,516

(22) Filed: Feb. 22, 2013

(65) Prior Publication Data

US 2013/0244932 A1 Sep. 19, 2013

Related U.S. Application Data

(60) Provisional application No. 61/602,837, filed on Feb. 24, 2012.

(51) Int. Cl.

| | |
|---|---|
| *A61K 38/00* | (2006.01) |
| *A61K 8/28* | (2006.01) |
| *A61K 38/26* | (2006.01) |
| *A61P 5/50* | (2006.01) |
| *A61P 3/08* | (2006.01) |
| *A61P 3/10* | (2006.01) |
| *A61P 7/12* | (2006.01) |
| *C07K 14/605* | (2006.01) |
| *A61K 31/18* | (2006.01) |
| *A61K 31/404* | (2006.01) |
| *A61K 31/4985* | (2006.01) |

(52) U.S. Cl.
CPC ............ *A61K 31/18* (2013.01); *A61K 31/404* (2013.01); *A61K 31/4985* (2013.01); *A61K 38/26* (2013.01)

(58) Field of Classification Search
None
See application file for complete search history.

(56) References Cited

U.S. PATENT DOCUMENTS

| | | | | |
|---|---|---|---|---|
| 2008/0200568 | A1* | 8/2008 | Chissoe | 514/789 |
| 2008/0261922 | A1* | 10/2008 | Carley et al. | 514/75 |
| 2008/0300170 | A1* | 12/2008 | Gelber et al. | 514/3 |
| 2011/0092510 | A1* | 4/2011 | Klein et al. | 514/249 |

OTHER PUBLICATIONS

"Synergism", available online at http://www.thefreedictionary.com/p/Synergistic%20effect, 2 pages (2014).*
Fineman et al., Diabetes/Metabolism Res. Rev. 20:411-417 (2004).*
Serajuddin, Adv. Drug Del. Rev. 59:603-616 (2007).*
Jones, R.L. et al., "Prostanoid receptor antagonists: development strategies and therapeutic applications", 2008, British Journal of Pharmacology, vol. 158, pp. 104-145.
O'Connell, M. et al., "Perisubstituted hexahyro-indolones as novel, potent and selective human EP3 receptor antagonists", 2009, Bioorganic & Medicinal Chemistry Letters, vol. 19, pp. 778-782.
Mishra, R. K and J. Singh, "Generation, Validation, and Utilization of a Three-Dimensional Pharmacophore Model for EP3 Antagonists", 2010, J. Chem. Inf. Model., vol. 50, pp. 1502-1509.
Meng, Z.X. et al., "Prostaglandin E2 regulates Foxo activity via the Akt pathway: implications for pancreatic islet beta cell dysfunction" 2006, Diabetologia, vol. 49, pp. 2959-2968.
Keller, M. P. et al., "A gene expression network model of type 2 diabetes links cell cycle regulation in islets with diabetes susceptibility", 2008, Gene Research, vol. 18, pp. 706-716.
Juteau, H. et al , "Structure-Activity Relationship of Cinnamic Acylsulfonamide Analogues on the Human EP3 Prostanoid Receptor", 2001, Bioorganic & Medicinal Chemistry Letters, vol. 9, pp. 1977-1984.
Juteau, H. et al ., "Structure-activity relationship on the human EP3 Prostanoid receptor by use of solid support chemistry" 2001, Bioorganic & Medicinal Chemistry Letters , vol. 11, pp. 747-749.
Belley, M. et al., "Comparision between two classes of selective EP3 antagonists and their biological activities", 2006, Bioorganic & Medicinal Chemistry Letters, vol. 16, pp. 5639-5642.
Takasaki, I. et al., "Involement of cyclooxygenase-2 and EP3 prostaglandin receptor in acute herpetic but not postherpetic pain in mice", 2005, Neuropharmacology, vol. 49, pp. 283-292.
Jin, J. et al., "Novel 3-Oxazolidinedione-6-aryl-pyridinones as Potent, Selective, and Orally Active EP3 Receptor Antagonists", 2010, ACS: Medicinal Chemistry Letters, vol. 1, pp. 316-320.
Zhou, N. et al., "1,7-Disubstituted oxyindoles are potent and selective EP3 receptor antagonists", 2010, Bioorganic & Medicinal Chemistry Letters, vol. 20, pp. 2658-2664.
Zhou, N. et al., "3,4-Disubstituted indole acylsulfonamides: a novel series of potent and selective human EP3 receptor antagonists", 2009, Bioorganic & Medicinal Chemistry Letters, vol. 19, 123-126.
Zhou, N. et al., "3-acrylamide-4-aryloxyindoles: Synthesis, biological evaluation and metabolic stability of potent and selective EP3 receptor antagonists", 2009, Bioorganic & Medicinal Chemistry Letters, vol. 19, 1528-1531.
Hategan, G. et al. ,"Heterocyclic 1,7-disubstituted indole sulfonamides are potent and selective human EP3 receptor antagonists", 2009, Bioorganic & Medicinal Chemistry Letters, vol. 19, 6797-6800.
Singh, J. et al., "Antagonists of the EP3 Receptor for Prostaglandin E2 Are Novel Antiplatelet Agents That Do Not Prolong Bleeding", 2008, ACS: Chemical Biology, vol. 4, No. 2, pp. 115-126.
Li,Y.H. et al., "3-Urea-1-(phenylmethyl)-pyridones as novel, potent, and selective EP3 receptor antagonists", 2010, Bioorganic & Medicinal Chemistry Letters, vol. 20, pp. 6744-6747.
Morales-Ramos, A. I. et al., "Structure-activity relationship studies of novel 3-oxazolidinedione-6-naphthyl-2-pyridinones as potent and orally bioavailable EP3 receptor antagonists", 2011, Bioorganic & Medicinal Chemistry Letters, vol. 21, pp. 2806-2811.

(Continued)

*Primary Examiner* — James H Alstrum Acevedo
*Assistant Examiner* — Thea D'Ambrosio
(74) *Attorney, Agent, or Firm* — Quarles & Brady LLP

(57) ABSTRACT

Provided herein are methods for increasing insulin secretion from beta cells. Also provide herein are methods comprising administering to a subject in need of increased insulin secretion a composition comprising a compound that directly or indirectly activates adenylate cyclase and an E prostanoid 3 (EP3) receptor antagonist that attenuates G alpha-i-subfamily (GSIS)-mediated adenylate cyclase inhibition.

19 Claims, 12 Drawing Sheets

(56) References Cited

OTHER PUBLICATIONS

Hilfiker, M.A. et al., "Discovery of novel aminothiadiazole amides as selective EP3 receptor antagonists", 2009, Bioorganic & Medicinal Chemistry Letters, vol. 19, pp. 4292-4295.

Belley, M. et al., "Structure-activity relationship studies on ortho-substituted cinnamic acids, a new class of selective EP3 antagonists", 2005, Bioorganic & Medicinal Chemistry Letters, vol. 15, pp. 527-530.

Gallant, M. et al., "Structure-activity relationship of biaryl acylsulfonamide analogues on the human EP(3) prostanoid receptor", 2002, Bioorganic & Medicinal Chemistry Letters, vol. 12, pp. 2583-2586.

Aschner, P. et al., "Effect of the Dipeptidyl Peptidase-4 Inhibitor Sitagliptin as Monotherapy on Glycemic Control in Patients With Type 2 Diabetes", 2006, Diabetes Care, vol. 29, No. 12, pp. 2632-2637.

Raz, I. et al., "Efficacy and safety of the dipeptidyl peptidase-4 inhibitor sitagliptin as monotherapy in patients with type 2 diabetes mellitus", 2006, Diabetologia, vol. 49, pp. 2564-2571.

Nonaka, K. et al., "Efficacy and safety of sitagliptin monotherapy in Japanese patients with type 2 diabetes", 2008, Diabetes Research and Clinical Practice, vol. 79, pp. 291-298.

Kimple, M. et al., "A Role for Gz in Pancreatic Islet β-Cell Biology", 2005, J. Biol. Chem., vol. 280, No. 36, pp. 31708-31713.

Kimple, M. et al., "Gαz Negatively Regulates Insulin Secretion and Glucose Clearance", 2009, J. Biol. Chem., vol. 283, No. 8, pp. 4560-4567.

\* cited by examiner

FIG. 4

A  Ptger3 promoter

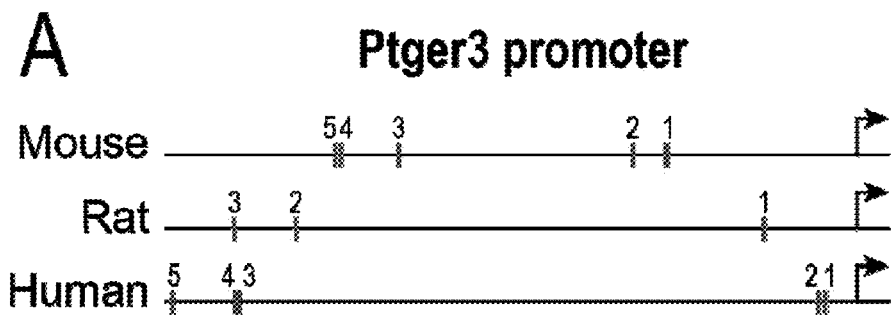

B  ChREBP binding sites

| | | E-box | E-box | base pair | |
|---|---|---|---|---|---|
| Mouse | 1 | CACTTGcctaaCATGTG | | 1802 - 1829 | SEQ ID NO. 1 |
| | 2 | CACTAGgaaagCAGAAG | | 2132 - 2148 | SEQ ID NO. 2 |
| | 3 | CAAAAGcaattCAAGTG | | 4368 - 4384 | SEQ. ID NO. 3 |
| | 4 | CAAGATcttgcCAGGTG | | 4961 - 4977 | SEQ ID NO. 4 |
| | 5 | CAGGTGgccttCACCAG | | 4972 - 4988 | SEQ ID NO. 5 |
| Rat | 1 | CAGATGcccttCAACAG | | 868 - 884 | SEQ ID NO. 6 |
| | 2 | CAAAAGcaattCAAGTG | | 5338 - 5354 | SEQ ID NO. 7 |
| | 3 | CACGTGtccttCACCAG | | 5931 - 5947 | SEQ ID NO. 8 |
| Human | 1 | CAGGTGcgcctCgGCAG | | 290 - 306 | SEQ ID NO. 9 |
| | 2 | CtAAAGgacttCAGGAG | | 363 - 379 | SEQ ID NO. 10 |
| | 3 | CtGTTGatactCAAGAG | | 5890 - 5906 | SEQ ID NO. 11 |
| | 4 | CtGCTGagccaCAGGAG | | 5931 - 5947 | SEQ ID NO. 12 |
| | 5 | CACGTcggctcCACCTG | | 6530 - 6546 | SEQ ID NO. 13 |

L-798,106

N-[(5-Bromo-2-methoxyphenyl)sulfony1]-3-[2-(2-naphthalenylmethyl)phenyl]-2-propenamide

DG-041

(2E)-3-[l-[(2,4-dichlorophenyl)methyl]-5-fluoro-3-methyl-lH-
indol-7-yl]-N-[(4,5-dichloro-2-thienyl)sulfonyl]-2-propenamide

SEQUENCE LISTING

```
<160> NUMBER OF SEQ ID NOS: 13

<210> SEQ ID NO 1
<211> LENGTH: 17
<212> TYPE: DNA
<213> ORGANISM: Mus musculus

<400> SEQUENCE: 1
cacttgccta acatgtg                                                      17

<210> SEQ ID NO 2
<211> LENGTH: 17
<212> TYPE: DNA
<213> ORGANISM: Mus musculus

<400> SEQUENCE: 2
cactaggaaa gcagaag                                                      17

<210> SEQ ID NO 3
<211> LENGTH: 17
<212> TYPE: DNA
<213> ORGANISM: Mus musculus

<400> SEQUENCE: 3
caaaagcaat tcaagtg                                                      17

<210> SEQ ID NO 4
<211> LENGTH: 17
<212> TYPE: DNA
<213> ORGANISM: Mus musculus

<400> SEQUENCE: 4
caagatcttg ccaggtg                                                      17

<210> SEQ ID NO 5
<211> LENGTH: 17
<212> TYPE: DNA
<213> ORGANISM: Mus musculus

<400> SEQUENCE: 5
```

```
caggtggcct tcaccag                                                    17

<210> SEQ ID NO 6
<211> LENGTH: 17
<212> TYPE: DNA
<213> ORGANISM: Rattus norvegicus

<400> SEQUENCE: 6
cagatgccct tcaacag                                                    17

<210> SEQ ID NO 7
<211> LENGTH: 17
<212> TYPE: DNA
<213> ORGANISM: Rattus norvegicus

<400> SEQUENCE: 7
caaaagcaat tcaagtg                                                    17

<210> SEQ ID NO 8
<211> LENGTH: 17
<212> TYPE: DNA
<213> ORGANISM: Rattus norvegicus

<400> SEQUENCE: 8
cacgtgtcct tcaccag                                                    17

<210> SEQ ID NO 9
<211> LENGTH: 17
<212> TYPE: DNA
<213> ORGANISM: Homo sapiens

<400> SEQUENCE: 9
caggtgcgcc tcggcag                                                    17

<210> SEQ ID NO 10
<211> LENGTH: 17
<212> TYPE: DNA
<213> ORGANISM: Homo sapiens

<400> SEQUENCE: 10
ctaaaggact tcaggag                                                    17

<210> SEQ ID NO 11
<211> LENGTH: 17
<212> TYPE: DNA
<213> ORGANISM: Homo sapiens

<400> SEQUENCE: 11
ctgttgatac tcaagag                                                    17

<210> SEQ ID NO 12
<211> LENGTH: 17
<212> TYPE: DNA
<213> ORGANISM: Homo sapiens

<400> SEQUENCE: 12
ctgctgagcc acaggag                                                    17

<210> SEQ ID NO 13
<211> LENGTH: 17
<212> TYPE: DNA
<213> ORGANISM: Homo sapiens
```

-continued

```
<400> SEQUENCE: 13
cacgtcggct ccacctg                                                      17
```

E-PROSTANOID RECEPTOR, PTGER3, AS A NOVEL ANTI-DIABETIC THERAPEUTIC TARGET

CROSS-REFERENCE TO RELATED APPLICATION

This application claims the benefit of U.S. Provisional Application No. 61/602,837, filed on Feb. 24, 2012, which is incorporated by reference herein in its entirety.

STATEMENT REGARDING FEDERAL SPONSORED RESEARCH OR DEVELOPMENT

This invention was made with government support under DK066369, DK058037, and DK080845 awarded by the National Institutes of Health. The government has certain rights in the invention.

BACKGROUND OF THE INVENTION

Type 2 diabetes mellitus (T2D) is a disease in which a person has high blood sugar as a result of resistance of the body's tissues to the glucose-lowering effects of insulin and failure of the beta cells of the islets of Langerhans to produce enough insulin. The American Diabetes Association reports that there are 18.8 million Americans with diagnosed T2D, 7.0 million individuals with undiagnosed T2D, and another 79 million potential candidates with pre-diabetes. An annual expenditure of $174 billion is attributed to the disease; this figure from 2007 is expected to rise. Complications of T2D are the third leading cause of death in the United States; in 2007 T2D was listed as a contributing factor to over 200,000 deaths. Prolonged untreated diabetes leads to heart diseases, stroke, kidney disease, blindness, and loss of limbs from advanced peripheral vascular disease. Combined, these facts underscore the critical need for increased understanding of and treatments for T2D.

The standard of care for T2D management in children and adults is healthy eating, portion control, increased physical activity, and glucose-lowering medications. However, few of the available medications have been approved for use in children or adolescents; thus, physicians are hesitant to prescribe these medications, and in doing so, fail to prevent further beta cell destruction if hyperglycemia persists.

Obesity is a risk factor for T2D because it is usually associated with insulin resistance. However, although most people with T2D are obese, most obese people do not develop T2D because they compensate for insulin resistance by secreting more insulin. When obese people progress to develop T2D, it is because their beta cells are unable to satisfy the increased demand for insulin. Thus, most of the newer T2D treatments in the clinic or under development target beta cell dysfunction and not insulin sensitivity.

Drugs that target G protein complexes are used as T2D therapeutics. GTP-binding proteins (G proteins) are membrane-associated signaling molecules whose activity is regulated by the cycle of GTP binding (active state) and GTP hydrolysis to GDP (inactive state), followed by GDP dissociation and re-binding of GTP. Heterotrimeric G proteins are composed of a beta-gamma-dimer and a catalytically-active alpha-subunit that are tightly associated with a transmembrane G protein-coupled receptor (GPCR) in their inactive state. Upon activation by receptor-ligand interaction these G protein-GPCR complexes dissociate in order to transmit signals to downstream effectors (i.e., signal transduction).

Of the four subfamilies of heterotrimeric G protein alpha-subunits (G alpha-s, G alpha-i, G alpha-q, and G alpha-12), only those in the G alpha-s subfamily can positively regulate the catalytic activity of adenylate cyclase, increasing the conversion of ATP to cAMP. cAMP is a known potentiator of beta cell function, having been shown to augment glucose-stimulated insulin secretion (GSIS) by numerous mechanisms (Lang, Eur. J. Biochem. 259:3-17 (1999); Furman and Pyne, Curr. Opin. Investig. Drugs 7:898-905 (2006); Shibasaki et al., Proc. Natl. Acad. Sci. USA 104:19333-19338 (2007)). Furthermore, cAMP has also been shown to have proliferative and anti-apoptotic effects on beta cells (Li et al., J. Biol. Chem. 278:471-478 (2003)).

Drugs that target a specific GPCR are widely used as T2D therapeutics. The hormone glucagon-like peptide 1 (GLP-1) is secreted by specialized cells in the intestine in response to the presence of nutrients from food. Sugars, proteins and fats can all cause GLP-1 release from the gut cells. GLP-1 activates a G alpha-s-coupled receptor on beta cells to stimulate cAMP production and potentiate GSIS from beta cells of the islets of Langerhans. Although GLP-1 is rapidly degraded by the enzyme dipeptidyl peptidase (DPP)-4, stable GLP-1 analogs exenatide (Byetta®, Lilly) and liraglutide (Victoza®, Novo-Nordisk) have been shown to be clinically effective for the treatment of T2D (Furman and Pyne (2006); Triplitt, Am. J. Manag. Care 13:S47-54 (2007)). In addition, inhibitors of DPP-4, including sitagliptin (Januvia®, Merck), saxagliptin (Onglyza®, Bristol-Myers Squibb), vildagliptin (Galvus®, Novartis), and linagliptin (Tradjenta®, Eli Lilly) also lead to improved beta cell function and glucose clearance in T2D patients (Furman and Pyne, supra; Triplitt, supra).

Of all the current diabetes therapeutics, agents that stimulate beta cell cAMP production, including DPP-4 inhibitors and GLP-1 analogs, are the only ones that positively impact beta cell replication, neogenesis, and/or survival in rodent models (Xu et al., Diabetes 48:2260-2276 (1999); Wang and Brubaker Diabetologia 45:1263-1273 (2002); Sturis et al., Br. J. Pharmacol. 140-123-132 (2003); Perfetti et al., Endocrinology 141:4600-4605 (2000); Gedulin et al., Endocrinology 146:2069-2076 (2005); Farilla et al., Endocrinology 143: 2069-2076 (2002)) or human islets (Farilla et al., Endocrinology 144:5149-5158 (2003)). Interestingly, GLP-1 treatment can protect both rodent and human beta cells from immune-mediated apoptosis (Sano et al., Biochem. Biophys. Res. Commun. 404:756-761 (2011); Pugazhenthi et al., Diabetologia 53:2357-2368 (2010)).

Unfortunately, not all diabetic patients respond to GLP-1-based treatments. Approximately 35-60% of diabetic patients treated with sitagliptin fail to achieve a glycosylated hemoglobin (i.e., HbAlc) target of <7% (Raz et al., Diabetologia 49:2564-2571 (2006); Aschner et al., Diabetes Care 29:2632-2637 (2006); Nonaka et al., Diabetes Res. Clin. Prac. 79:291-298 (2008)). HbAlc≥6.5% is a criterion for the diagnosis of diabetes, according to the American Diabetes Association. Further, there exists a controversy in the literature about whether agents that target GLP-1 action or breakdown also stimulate pancreatitis, a risk factor for the later development of pancreatic cancer (Anderson and Trujillo, Ann. Pharmacother. 44:904-909 (2010); Elashoff et al., Gastroenterology 141:150-156 (2011)).

There remains a need in the art for additional treatments for increasing insulin secretion from beta cells in individuals with T2D and in individuals at risk for developing T2D.

BRIEF SUMMARY

The invention relates generally to methods for increasing insulin secretion from beta cells and, more particularly, to methods comprising administering to a subject in need of increased insulin secretion a composition comprising a compound that activates adenylate cyclase and an E prostanoid 3 receptor antagonist that attenuates G alpha-i-subfamily (GSIS)-mediated adenylate cyclase inhibition. EP3 (gene symbol: Ptger3) is a cellular receptor for E-series prostanoids such as PGE1 and PGE2.

In one aspect, the present invention is summarized as a method for increasing insulin secretion from beta cells. The method includes the steps of administering to a subject in need of increased insulin secretion a composition comprising a compound that directly or indirectly activates adenylate cyclase and an E prostanoid 3 receptor antagonist that attenuates G alpha-i-subfamily (GSIS)-mediated adenylate cyclase inhibition. In some embodiments, the compound that leads to activation of adenylate cyclase is selected from the group consisting of a compound that activates a glucagon-like peptide-1 (GLP-1) receptor, a gastric inhibitory peptide (GIP) receptor, or a pituitary adenylate cyclase-activating peptide (PACAP) receptor. In some of these embodiments, the compound that activates the GLP-1 receptor is selected from the group consisting of DPP-4 inhibitors and incretin mimetics. In some embodiments, a compound that modulates EP3 is L-798,106. In other embodiments, an E prostanoid 3 receptor antagonist is DG-041 or another EP3 antagonist known in the art. In a preferred embodiment of the present invention, a compound that directly or indirectly activates adenylate cyclase is sitagliptin and an E prostanoid 3 receptor antagonist is L-798,106.

In a further aspect, the invention is summarized as a method of treating or preventing type II diabetes in an individual. The method includes the steps of administering to a subject in need of increased insulin secretion a comprising a compound that directly or indirectly activates adenylate cyclase and an E prostanoid 3 receptor antagonist that attenuates G alpha-i-subfamily (GSIS)-mediated adenylate cyclase inhibition. In some embodiments, the compound that directly or indirectly activates adenylate cyclase is selected from the group consisting of a compound that activates a glucagon-like peptide-1 (GLP-1) receptor, a gastric inhibitory peptide (GIP) receptor, or a pituitary adenylate cyclase-activating peptide (PACAP) receptor. In some of these embodiments the compound that activates the GLP-1 receptor is selected from the group consisting of DPP-4 inhibitors and incretin mimetics. In some embodiments, a compound that attenuates GSIS-mediated adenylate cyclase inhibition is L-798,106. In a preferred embodiment of the present invention, a compound that directly or indirectly activates adenylate cyclase is sitagliptin and the E prostanoid 3 receptor antagonist that attenuates GSIS-mediated adenylate cyclase inhibition is L-798,106.

In another aspect, the invention is summarized as a method of treating or preventing type I diabetes in an individual. The method includes the steps of administering to a subject in need of increased insulin secretion a compound that directly or indirectly activates adenylate cyclase and an E prostanoid 3 receptor antagonist that attenuates G alpha-i-subfamily (GSIS)-mediated adenylate cyclase inhibition by modulating EP3. In some cases, the method comprises administering to a subject in need of increased insulin secretion any pairwise combination of a compound that directly or indirectly activates adenylate cyclase and a compound that attenuates GSIS-mediated adenylate cyclase inhibition described herein. In some cases, the method comprises administering more than one compound that directly or indirectly activates adenylate cyclase or more than one E prostanoid 3 receptor antagonist that attenuates G alpha-i-subfamily (GSIS)-mediated adenylate cyclase inhibition by modulating EP3.

In a further aspect, the invention is summarized as a composition comprising a compound that directly or indirectly activates adenylate cyclase and an E prostanoid 3 receptor antagonist that attenuates G alpha-i-subfamily (GSIS)-mediated adenylate cyclase inhibition by modulating EP3. The composition can comprise any pairwise combination of a compound that directly or indirectly activates adenylate cyclase and a compound that attenuates GSIS-mediated adenylate cyclase inhibition described herein.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIG. 2A depicts fasting plasma glucose values in plasma samples obtained from B6 and BTBR mice at 4 and 10 weeks of age, when mice were either lean (L) or obese (O). Circles show individual mice (n=5 for each condition). Horizontal bars show mean+/−SEM. The convergence of strain, age and obesity revealed the diabetes-susceptible nature of BTBR mice. FIG. 2B depicts islet expression profiling of the same group of mice illustrated in FIG. 2A. 10-week-old BTBR-Ob mice were diabetic; all of the other mouse groups were non-diabetic. Diabetic BTBR-Ob mice were the only group that displayed significantly increased Ptger3 expression on an Agilent mouse gene microarray.

FIG. 4 depicts analyses of the gene promoters of the mouse, rat, and human Ptger3 gene. The genomic sequence 10,000 base pairs upstream of the transcription start site was used as the promoter region, and was manually analyzed in MatInspector (Genomatix) using the consensus sequences for carbohydrate response element binding protein (ChREBP) (E-boxes). The mouse and rat promoter sequences are conserved and contain two identical E-boxes. While the human promoter is not conserved among species, it contains at least five degenerate E-box sequences.

Figure 1:
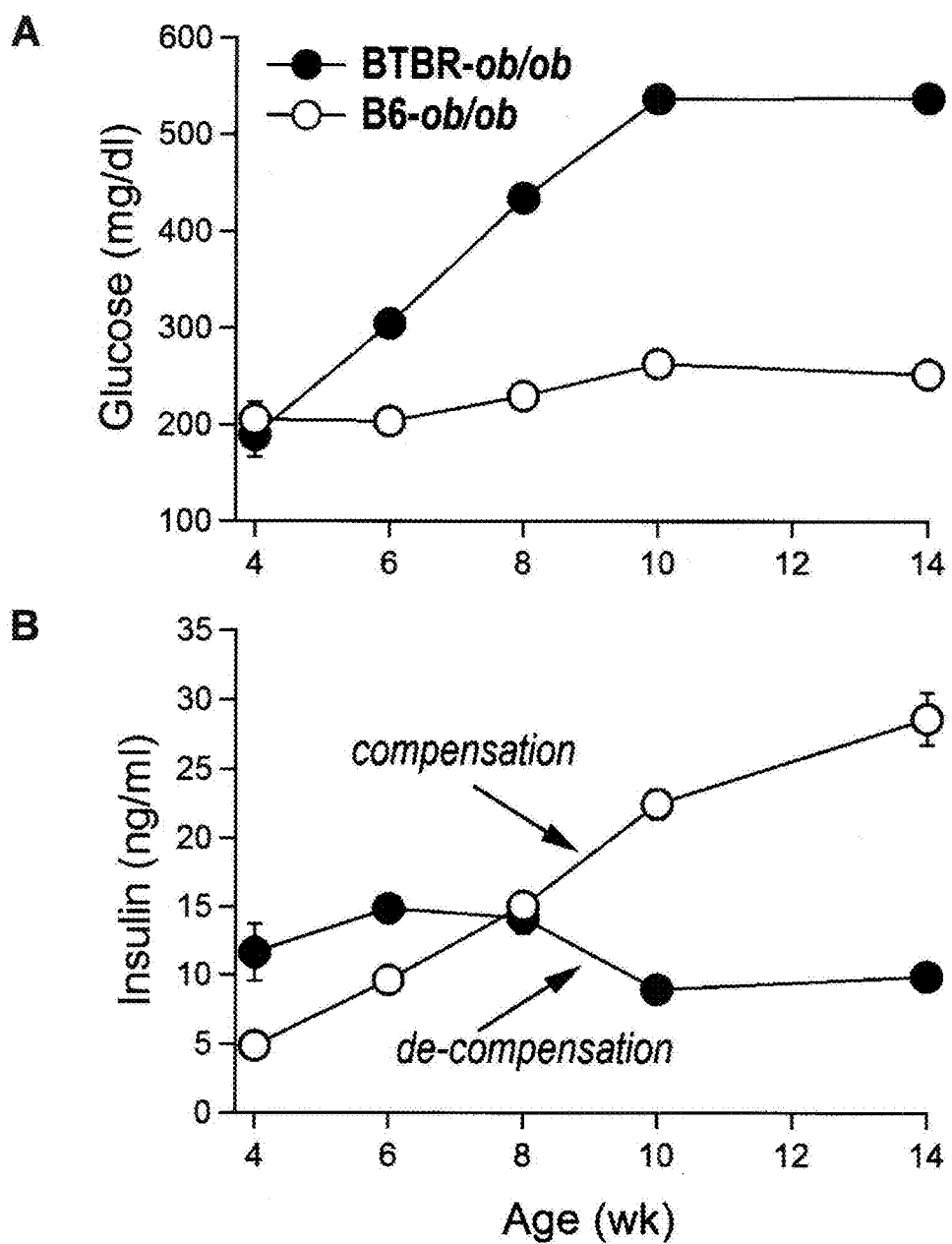
FIGS. 1A-B illustrate using BTBR-Ob mice as a model for identifying novel therapeutics that might prevent or reverse beta cell de-compensation in T2D. Depicted are fasting plasma glucose levels (A) and insulin levels (B) in plasma samples obtained from genetically obese (Leptin ob/ob) B6 and BTBR mice. Results are shown as a function of age in weeks.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DESCRIPTION OF THE INVENTION

Broadly, provided herein are methods for increasing insulin secretion from beta cells. More specifically, this document provides methods of administering to a subject in need of increased insulin a composition comprising a compound that leads to activation of adenylate cyclase and a compound that inhibits G alpha-i-mediated inhibition of adenylate cyclase by modulating EP3 activity (gene symbol: Ptger3). Dosage of the composition, and the agents in the composition, can be administered in an amount sufficient to achieve GSIS from beta cells at a level characteristic of that secreted by a beta cell obtained from a non-diabetic subject. One of skill in the art in possession of this disclosure can optimize the dosages as appropriate. The present invention is based, at least in part, on the Inventors' discovery that diabetes is associated with increased expression of Ptger3 in pancreatic islets. Through experiments described in the Examples below, the Inventors found that: (i) increased Ptger3 expression in diabetic mouse islet cells results in E-prostanoid-mediated negative regulation of insulin secretion from beta cells; and (ii) when EP3 activity is suppressed in islets from diabetic subjects, insulin secretion can be elevated to levels comparable to that observed from non-diabetic subjects. Further, the Inventors found that treating islets obtained from diabetic mice with both GLP-1 and an EP3 antagonist increased GSIS to a level higher than that achieved by treatment with either GLP-1 or the EP3 antagonist alone. This finding is particularly important given that T2D drugs that target the GLP-1 pathway are inefficacious in a significant portion of T2D patients (Raz et al., supra; Aschner et al., supra; Nonaka et al., supra).

The methods disclosed have valuable applications including treatment or prevention of type 1 diabetes (T1D) or T2D. In several aspects, the present invention involves increasing insulin secretion by increasing cyclic AMP (cAMP) production mediated by adenylate cyclase (AC). cAMP can positively impact both insulin secretion and, potentially, beta cell mass by activating beta cell proliferation, growth, and survival pathways. Some agents currently used to increase insulin secretion by increasing cAMP production target the GLP-1 pathway, which is known to activate AC in beta cells.

In contrast, the methods of the present invention increase insulin secretion by increasing cAMP production by targeting two pathways that modulate adenylate cyclase in beta cells: (i) a hormonal-mediated positive regulatory pathway, such as GLP-1, and (ii) the negative regulation mediated by the E prostanoid receptor EP3. The Inventors found that, when EP3 is activated in beta cells, insulin secretion from beta cells is inhibited, likely through cAMP. EP3 expression and/or E prostanoid production are elevated only in subjects with diabetes. Blocking EP3 activity (for example, using an EP3-specific antagonistic compound) enhances GSIS from diabetic pancreatic islets to a level characteristic of a non-diabetic islet. Advantageously, since EP3 expression and activity are only elevated in response to diabetes, molecules that are developed to inhibit Ptger3 should only be effective in diabetic patients, yielding a disease-specific drug profile.

The Inventors' observation that EP3 activity modulates GSIS, and the fact that EP3 can inhibit cAMP production in beta cells, are relevant to the disclosed method. Knowing that T2D drugs that target hormonal pathways such as GLP-1 that signal downstream to adenylate cyclase-mediated cAMP production in beta cells, the Inventors predicted that treating islets obtained from diabetic subjects with a composition containing both a compound that directly or indirectly activates adenylate cyclase and, in response, stimulates AC-mediated cAMP production in beta cells and a compound that inhibits EP3 activity would lead to increased GSIS from the treated islets. Without being bound to any particular theory, a composition described herein is effective for increasing GSIS in islets obtained from diabetic mice, at least in part because the adenylate cyclase-activating and EP3-inhibiting compounds of each composition simultaneously relieve a tonic inhibition on adenylate cyclase caused by increased endogenous E prostanoid signaling through increased EP3 receptor and also stimulate AC through the stimulatory GLP-1 receptor.

Adenylate cyclase is an enzyme capable of integrating positive and negative signals that act directly from G protein-coupled receptors (GPCRs) through stimulation of the G-protein alpha and beta/gamma subunits or indirectly via intracellular signaling by, for example, a calcium/calmodulin-dependent protein kinase (CaMK) or a Protein Kinase C(PKC) isoenzyme. As used herein, adenylate cyclase is "activated" when any process (e.g., a conformational change stimulated by a G-protein) initiates the activity of an inactive adenylate cyclase enzyme.

In some embodiments of the present invention, the methods can be used to treat diabetic subjects exhibiting sub-optimal GSIS in response to treatment with GLP-1 mimetics or DPP-4 inhibitors. As used herein, "sub-optimal" means that GSIS levels in the subject are lower than those exhibited by a non-diabetic subject. One of skill in the art can develop appropriate dosing regimens sufficient to balance adenylate cyclase-mediated cAMP production and subsequent insulin secretion using the methods of the present invention. GLP-1 mimetics suitable for use in the present invention include, but are not limited to exentatide, liraglutide, and taspoglutide. DPP-4 inhibitors suitable for use in the present invention include, but are not limited to sitagliptin, saxagliptin, vildagliptin, and linagliptin. In some embodiments of the present invention, the methods can be used to treat subjects who react adversely to GLP-1 mimetics or DPP-4 inhibitors. As used herein, "react adversely" means that the subject exhibits symptoms or characteristics, physiological or otherwise, that are unfavorable in terms of the subject's health. In such cases, the required effective amount of GLP-1 mimetics or DPP-4 inhibitors might be lower when administered in combination with a Ptger3 antagonist relative to administration of the former alone, at least in part because increasing the ratio of Ptger3 antagonist to GLP-1 agonist would likely result in increased insulin secretion from beta cells. One of skill in the art can develop appropriate dosing regimens for such situations.

It is contemplated that the present invention can also be practiced using a combination of an EP3 antagonist and a compound targeted to a hormonal pathway other than GLP-1 that stimulates adenylate cyclase-mediated cAMP production in beta cells. Examples of such hormones are gastric inhibitory polypeptide (GIP), pituitary adenylate cyclase-activating peptide (PACAP), and vasoactive intestinal peptide (VIP). Like GLP-1, GIP, PACAP, and VIP are classified as "incretins." Incretins function in beta cells to potentiate GSIS. Furthermore, receptors for GLP-1, GIP, PACAP, and VIP are in the same subfamily as the GLP-1 receptor (Subfamily B1 of the Secretin family of GPCRs, also referred to as Class B or Class 2). Thus, it is contemplated that any agent having the capacity to potentiate GLP-1 function in a cell could also potentiate other incretin functions in said cell if these incretin receptors were still expressed on the cell surface in the T2D state.

It is contemplated that in some cases the present invention can be practiced using any pairwise combination of a compound that directly or indirectly activates adenylate cyclase and a compound that attenuates GSIS-mediated adenylate cyclase inhibition described herein. For example, a method described herein can comprise administering to a subject in need of increased insulin secretion more than one compound that directly or indirectly activates adenylate cyclase. In some cases, the method can alternatively or additionally comprise administering to a subject in need of increased insulin secretion more than one E prostanoid 3 receptor antagonist that attenuates G alpha-i-subfamily (GSIS)-mediated adenylate cyclase inhibition by modulating EP3.

It is contemplated that the compositions of the present invention can be administered to subjects in need of increased insulin secretion from beta cells. The composition can be administered to the subject via an appropriate delivery route and device. One of skill in the art can develop appropriate dose delivery methods. The composition can be provided as part of a kit. Such a kit could include a composition as described and claimed herein and a delivery device to administer the composition to the subject. It is contemplated that the present invention can be practiced using a variety of EP3 antagonists. L-798,106 (5-Bromo-2-methoxy-N-[3-(2-naphthalen-2-ylmethyl-phenyl)-acryloyl]-benzenesulfonamide) is one EP3 antagonist that is exemplified herein. See, for example, Jones et al., *Fundam. Clin. Pharmacol.* 22 (Suppl. 2):P078, 2008; Clarke et al., *Br. J. Pharmacol.* 141:600-609, 2004. In some cases, other EP3 antagonists can be used to practice the methods provided herein. For example, DG-041 is an EP3 antagonist that can be used to practice the methods provided herein (Singh et al., *ACS Chem. Biol.* 4:115-126, 2009). Additional selective EP3 receptor ligands appropriate for use according to the methods provided herein are described in Juteau et al., *Bioorg. Med. Chem.* 9:1977-1984, 2001(a); Juteau et al., *Bioorg. Med. Chem. Lett.* 11:747-749, 2001(b); Belley et al., *Bioorg. Med. Chem. Lett.* 15:527-530, 2005; Belley et al., *Bioorg. Med. Chem. Lett.* 16:5639-5642, 2006; Jin et al., *ACS Med. Chem. Lett.* 1:316-320, 2010; Gallant et al., 2002 (*Bioorg. Med. Chem. Lett.* 12:2583-2586); Zhou et al., *Bioorg Med Chem. Lett.* 19:123-126, 2009(a); Zhou et al., *Bioorg. Med. Chem. Lett.* 19:1528-153, 2009(b); Zhou et al., *Bioorg. Med. Chem. Lett.* 20:2658-2664, 2010; O'Connell et al., *Bioorg. Med. Chem. Lett.* 19:778-782, 2009; Mishra and Singh, *J. Chem. Inf. Model.* 50:1502-1509, 2010; Hategan et al., *Bioorg. Med. Chem. Lett.* 19:6797-6800, 2009; Li et al., *Bioorg. Med. Chem. Lett.* 20:6744-6747, 2010; Morales-Ramos et al., *Bioorg. Med. Chem. Lett.* 21:2806-2811, 2011; Hilfiker et al., *Bioorg. Med. Chem. Lett.* 19:4292-4295, 2009, each of which is incorporated herein by reference as if set forth in its entirety.

The Inventors were the first to recognize that increased EP3 activity negatively modulates insulin secretion in pancreatic islets obtained from diabetic subjects. Previously, the Inventors profiled gene expression in six tissues of lean and obese B6 and BTBR mice before and after the onset of diabetes (Keller et al., *Genome Res.* 18:706-716 (2008)). Although it was not mentioned in Keller et al. (2008), data provided by the aforementioned study indicates that the expression level of the prostaglandin E receptor 3 (subtype EP3), encoded by Ptger3, is elevated >30-fold in the islets of diabetic BTBR mice relative to non-diabetic mice.

Prostaglandin E receptor 3 is a member of the G-protein coupled receptor family. It is one of four receptors identified for E-series prostanoids such as PGE1 and PGE2, and the only receptor that couples primarily to G alpha i-subfamily proteins. In a rat-derived beta cell line, the endogenous E prostanoid receptor signals exclusively through G alpha-z, a member of the G alpha-i subfamily of heterotrimeric G proteins, to block insulin secretion (Kimple et al., *J. Biol. Chem.* 280:31708-31713 (2005)). Because of the observed negative effect of PGE1 on insulin secretion, the identity of the E prostanoid receptor was presumed to be EP3. Further, loss of expression of G alpha-z caused constitutive increases in pancreatic islet cAMP production and GSIS (Kimple et al., *J. Biol. Chem.* 283:4560-4567 (2008)), suggesting a role for G alpha-i-subfamily signaling in regulating pancreatic beta cell function and biology. In view of this information and the finding that Ptger3 expression is upregulated in the islets of diabetic mice relative to non-diabetic mice, the Inventors hypothesized that a PGE2-EP3-G alpha-i pathway is upregulated in animals with T2D. Thus, dysfunctional signaling by the PGE2-EP3-G alpha-i subfamily pathway caused by increased expression of the receptor could negatively affect cAMP production, leading to diminished beta cell function and mass. The Inventors hypothesized that antagonism of the EP3 receptor might prevent or reverse the beta cell pathobiology characteristic of T2D.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

In describing the embodiments and claiming the invention, the following terminology will be used in accordance with the definitions set out below.

As used herein, "about" means within 5% of a stated concentration range or within 5% of a stated time frame.

As used herein, "administering" or "administration" includes any means for introducing a compound of the present invention into the body, preferably into the systemic circulation. Examples include but are not limited to oral, nasal, otic, ophthalmic, buccal, sublingual, pulmonary, transdermal, transmucosal, as well as subcutaneous, intraperitoneal, intravenous, epidural and intramuscular injection.

As used herein, "agonist" means a chemical, compound, or molecule that binds to a cellular receptor and activates it to cause a response. Agonists can be naturally occurring or chemical mimics.

As used herein, "analog" means a chemical mimic of a naturally-occurring agonist. As drugs, analogs might be used for many reasons, including, but not limited to, increased stability, longevity, activation of a cellular receptor, or access to/restriction from a particular body tissue.

As used herein, "antagonist" means a chemical, compound or molecule that binds to a cellular receptor but does not provoke the biological response seen when an agonist binds to the receptor. Antagonists can compete with agonists for binding to the same site on the receptor, or might bind to a separate site, causing the receptor to undergo changes that preclude agonist binding. Antagonists can be used therapeutically to block an overactive agonist/receptor interaction that is causing an undesired biological consequence.

As used herein, "effective amount" means an amount of an agent sufficient to evoke a specified cellular effect according to the present invention.

As used herein, "obesity" means a medical condition in which excess body fat has accumulated to the extent that it may have a negative effect on health. One measurement of body fat is the body mass index (BMI), a measurement that compares weight and height, defines obesity as greater than 30 kg (weight) per $m^2$ (height$^2$). Obesity increases the likelihood of various diseases, particularly heart disease and T2D.

A "therapeutically effective amount" means an amount of a compound that, when administered to a subject for treating a disorder, condition, or disease, is sufficient to effect such treatment for the disorder, or condition, or disease. The "therapeutically effective amount" will vary depending on the compound, the disorder, or condition, or disease state being treated, the severity or the disorder, or condition, or disease treated, the age and relative health of the subject, the route and form of administration, the judgment of the attending medical or veterinary practitioner, and other factors.

For purposes of the present invention, "treating" or "treatment" describes the management and care of a patient for the purpose of combating the disease, condition, or disorder. The terms embrace both preventative, i.e., prophylactic, and palliative treatments. Treating includes the administration of a compound of present invention to prevent the onset of the symptoms or complications, alleviating the symptoms or complications, or eliminating the disease, condition, or disorder.

The invention will be more fully understood upon consideration of the following non-limiting Examples. It is specifically contemplated that the methods disclosed are suited for treatment of Types I and II Diabetes generally. All papers and patents disclosed herein are hereby incorporated by reference as if set forth in their entirety.

EXAMPLES

Example 1

Materials and Methods

Animals. C57Bl/6 and BTBR mice, both lean and harboring the Leptin$^{Ob}$ mutation, were derived from in-house breeding colonies in the University of Wisconsin Biochemistry Department, as described in Keller et al. (2008).

Plasma Measurements. Blood samples were collected by retroorbital puncture from mice fasted for 4 hours (8 am-noon) in EDTA-coated tubes to generate plasma samples. Plasma glucose was measured by the glucose oxidase method using a commercially available kit (Sigma-Aldrich). For lean mice, insulin was measured by radioimmunoassay (RIA; RI-13K, Linco Research). For ob mice, insulin was measured by an in-house developed ELISA using a pair of anti-insulin/proinsulin antibodies (clones D6C4 and D3E7-BT) purchased from Research Diagnostics. Briefly, half-area 96-well high-binding plates (Corning) were coated overnight with 3 µg/mL D6C4/PBS to a total volume of 50 µL/well. After aspiration of D6C4, plates were blocked with PBS containing 4% RIA-grade BSA (Sigma) for 1 hour (100 µL/well) and then incubated for 1 hour with 25 µL insulin standards (Linco Research, 0.1-10 ng/mL) or plasma samples. 25 µl D3E7-BT, at 1 µg/ml in PBS/1% BSA was added, gently mixed, and incubated for an additional hour. After washing each well three times with wash buffer (50 mM Tris, 0.2% Tween-20, pH 8.0), 1 µg/mL of streptavidin-HRP (Pierce) in PBS/0.1% BSA was added (50 µL/well) and incubated for 30 minutes. Following an additional three washes, 16 µmol/mL of o-phenylenediamine (Sigma), dissolved in citrate buffer (0.1 M citrate-phosphate, 0.03% $H_2O_2$ at pH 5.0), was added (50 µL/well) and incubated for 30 minutes, followed by an equal volume of 0.18 M sulfuric acid to quench the reaction. Absorbance at 492 nm was determined by a plate reader (Ultra 384 TECAN).

Mouse Islet Isolation & Culture. Intact pancreatic islets were isolated from 10-12-week-old BTBR lean and ob/ob mice using a known collagenase digestion protocol (Rabaglia et al., *Am. J. Physiology Endo. Metab.* 289:E218-224 (2005)). Instead of $CO_2$ asphyxiation and decapitation, mice were Avertin-anesthetized and exsanguinated immediately prior to cannulation of the bile duct and inflation of the pancreas with a collagenase solution. Islets were cultured overnight in 5 ml RPMI 1640 containing 11.1 mM glucose and 10% heat-inactivated FBS with 1X penicillin/streptomycin prior to in vitro assay for insulin secretion and PGE2 production.

Mouse Islet Insulin Secretion and PGE2 Production Assays. Insulin secretion assays were performed in mesh-bottomed glass tubes essentially as in Rabaglia et al. (2005). Modifications include: 4 islets/replicate were picked into Krebs Ringer Bicarbonate Buffer (KRBB) containing 1.7 mM glucose and 0.25% BSA. Replicates were pre-incubated for 1 hour in fresh 1.7 mM KRBB before being transferred to stimulation medium containing the desired concentrations of glucose and drug treatment (e.g., PGE1, PGE2, and sulprostone [Sigma Aldrich] or L-798,106 [Tocris]). Insulin secretion as a percentage of total insulin content was determined using an in-house insulin ELISA, as described above.

The Prostaglandin $E_2$ EIA Kit (Monoclonal) was obtained from Cayman Chemical Company. Overnight culture medium was subjected to PGE2 concentration analysis as recommended in the manufacturer's protocol. Media samples were diluted 1:2 in assay buffer before analysis. PGE2 concentration was normalized to the total number of cultured islets and the incubation time to obtain PGE2 production/islet/h.

Human Islet Culture and Insulin Secretion Assays. Human islets were obtained through the Integrated Islet Distribution Program. On the day of arrival, islets were cultured overnight in RPMI containing 8 mM glucose, 10% heat-inactivated FBS, and 1X penicillin/streptomycin to confirm viability and sterility. Islets were cultured in 6 cm Petri dishes with approximately 1000 islet equivalents plated per dish. Islets were hand-picked and incubated an additional day in medium containing the desired concentration of glucose and/or xylitol before assaying for insulin secretion. Insulin secretion assays on human islets were performed identically to those described for mouse islets, except that 10 islets were used per replicate instead of 4.

INS1 Cell Culture and Insulin Secretion Assays. The glucose responsive rat beta cell line, INS1 (832/3) was cultured in RPMI 1640 (11.1 mM glucose) supplemented with $NaHCO_3$, HEPES, heat-inactivated FBS, L-glutamine, sodium pyruvate and β-mercaptoethanol. 3 days prior to assay, $1 \times 10^5$ cells were plated per well in 96-well cell culture plates. Twenty-four hours prior to the assay, the medium was aspirated and fresh growth medium added. On the day of the assay, confluent Ins-1 832/3 cells were washed once with sterile PBS and pre-incubated for 2 hours in KRBB supplemented with 25 mM HEPES and containing 1.7 mM glucose and 0.2% BSA. Cells were then stimulated for 2 hours with KRBB containing 16.7 mM glucose and the desired concentrations of agonists/antagonists. Secretion buffer was collected and the secreted and cellular insulin content determined by acid/ethanol extraction, as described above.

Quantitative Real-Time PCR. cDNA was generated from islet RNA samples obtained from lean and obese 10-week old C57B1/6 as described in as described in Keller et al., (2008). Four nanograms (ng) of template cDNA was subjected to a PCR cycling protocol (95 degrees C., 10 min; 40 cycles of 95 degrees, 30 sec.; 55 degrees, 30 sec.; and 68 degrees, 30 sec.) using Sybr Green as a read-out for double stranded DNA production. Fluorescence was measured during the 68 degree extension step. The threshold for fluorescence detection was set automatically using the instrument control software (Applied Biosystems). Gene-specific primers were designed and ordered from IDT. Primers against mouse β-actin were used in separate reactions as the housekeeping gene control. Ptger3 mRNA expression was represented as the difference in cycle times between the β-actin and Ptger3 primer sets. Melting curves and 1.5% agarose gels of PCR products were performed to ensure primer efficiency and specificity.

Statistical Analysis. Data are expressed as means+/−standard error of the means when applicable. Statistical significance was judged by computing a Student's t-test, with a threshold for significance of $p<0.05$.

Example 2

Genetics Determine Diabetes Susceptibility

A murine model of T2D was generated by utilizing two mouse strains that differ in their susceptibility to obesity-induced diabetes, caused by beta cell decompensation. The C57B1/6 (B6) mouse strain is diabetes-resistant when challenged with morbid obesity imposed by the Leptin$^{Ob}$ mutation. In contrast, BTBR mice develop severe diabetes in response to the same obesity challenge, resulting in blood glucose levels that can exceed 600 mg/dL.

Strain-dependent differences in diabetes susceptibility in B6 and BTBR mice were exploited to identify key regulatory genes expressed in pancreatic islets that might contribute to the pathogenesis of T2D. Under fasting conditions, genetically obese B6 mice maintain euglycemia due to a large compensatory increase in plasma insulin (FIGS. 1A-B). In contrast, BTBR mice develop severe diabetes, beginning as early as 6 weeks of age, eventually leading to beta cell decompensation (FIGS. 1A-B).

Previously, the Inventors have shown that mechanistically, islets from BTBR-Ob mice are unable to mount the increase in islet function and mass necessary to compensate for the insulin resistance resulting from morbid obesity, eventually leading to beta cell decompensation (Clee et al., *Am. J. Ther.* 12:491-498 (2005)). Further, the Inventors showed that whole pancreas insulin content, a measure of beta cell mass, is reduced by ~80% in diabetic BTBR-Ob mice compared with non-diabetic B6-Ob mice. This loss in beta cell mass underlies an inability to secrete sufficient insulin to properly regulate blood glucose. Uncontrolled blood glucose levels ultimately leads to beta cell death.

Figure 2:
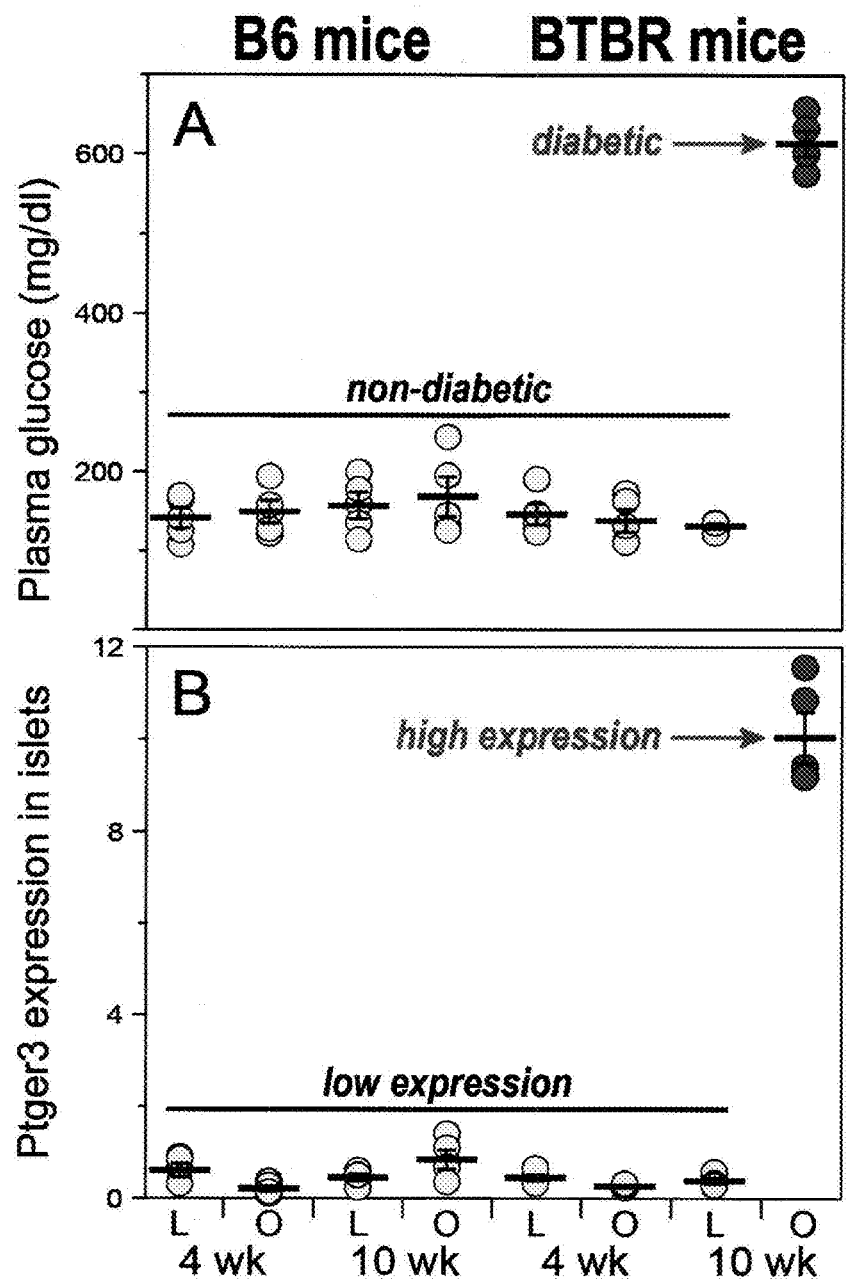
FIGS. 2A-B illustrate that diabetes and Ptger3 gene expression are highly correlated.

Collectively, the results shown in FIG. 1, FIG. 2A, and in Clee et al. (2005) suggest that BTBR-Ob mice are an ideal model for the identification of novel therapeutics that might prevent or reverse beta cell decompensation in T2D.

Example 3

Diabetes and Ptger3 Expression are Highly Correlated

Figure 3:
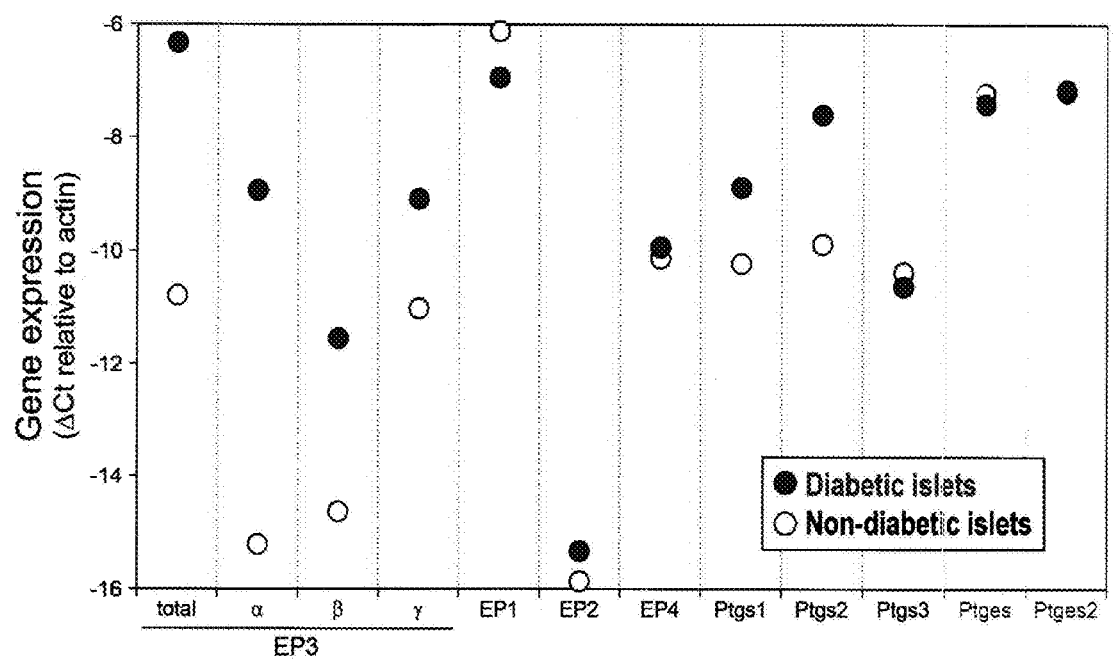
FIG. 3 illustrates that both the receptor for E prostanoids (EP3) and the enzymes responsible for their synthesis are up-regulated in diabetic islets. Quantitative real-time (qRT) PCR was performed on cDNA samples generated from non-diabetic and diabetic mouse islets. EP3 total represents a primer set to a region common in all three splice variants (alpha, beta, and gamma), all of which were elevated in diabetic islets. Also tested were primers against the other E prostanoid receptors (EP1, EP2, and EP4). Primers against the prostaglandin-endoperoxidase synthases (Ptgs1, Ptgs2, and Ptgs3), as well as the prostaglandin E synthases (Ptges and Ptges2) were also tested. The expression of both Ptgs1 and Ptgs2, the rate limiting step in PGE2 synthesis from arachidonic acid, are both elevated in diabetic islets.

Previously, the Inventors profiled gene expression in six tissues of surveyed gene expression of lean and obese B6 and BTBR mice aged 4 weeks and 10 weeks, before and after the onset of diabetes (Keller et al., 2008) (FIG. 2A). The focus of the 2008 publication was a group of genes related to progression through the cell cycle, thus explaining possible differences in diabetes susceptibility between the B6-Ob and BTBR-Ob mouse strains. Recent analysis of the islet gene expression profiling provided by Keller et al. (2008) indicated that the gene expression level of an isoform of a G protein coupled receptor, Ptger3, is greatly elevated in the islets of diabetic BTBR mice relative to non-diabetic mice (FIG. 2B). Quantitative real-time (qRT) PCR confirmed that Ptger3 mRNA expression is increased significantly in 10 week-old diabetic BTBR mice relative to lean BTBR mice. Further, all three mouse Ptger3 mRNA splice variants ($\alpha$, $\beta$, and $\gamma$) were elevated >30-fold ($p<10-8$) in response to diabetes (FIG. 3). These mRNA splice variants encode proteins EP3$\alpha$, EP3$\beta$, and EP3$\gamma$ that are 90% identical, varying only in the C-terminal tail. Each of the mouse EP3 variants can couple to inhibitory G proteins of the G alpha-i subfamily, which, when stimulated in the $\beta$-cell, would result in a net inhibition of GSIS.

Extreme hyperglycemia is a pathological phenotype of T2D in BTBR mice. Accordingly, the Inventors analyzed the promoter of the mouse Ptger3 gene for carbohydrate response elements (i.e., E-boxes) that are activated by carbohydrate response element binding protein (ChREBP, also referred to as MLXIPL, a basic helix-loop-helix transcription factor of the Myc/Max/Mad superfamily (Minn et al., *Endocrinology*. 146:2397-2405 (2005)). The murine Ptger3 promoter contains four consensus ChREBP binding sites, which might explain the increased Ptger3 mRNA expression exhibited by diabetic mice (FIG. 4). Similar analyses of rat and human Ptger3 gene promoters reveal three consensus E-boxes in the rat promoter and five degenerate E-boxes in the human promoter.

Example 4

Figure 5:
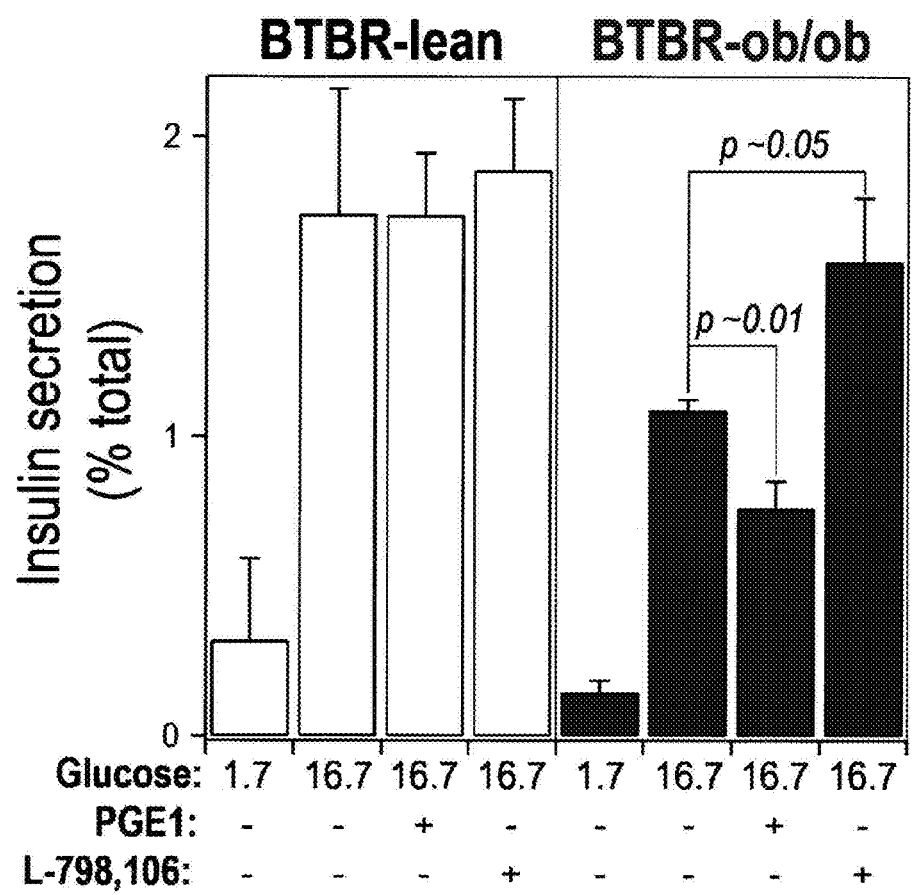
FIG. 5 illustrates that a Ptger3 antagonist can normalize insulin secretion from islets obtained from diabetic mice. Insulin secretion from islets isolated from either 10 week old lean (non-diabetic; left side, unshaded bars) or ob/ob (diabetic; right side, shaded bars) BTBR mice. High glucose (16.7 mM) was used to stimulate insulin secretion in the absence (−) or presence (+) of the EP3-selective agonist PGE1 (5 µM), or the EP3-specific antagonist L-798,106 (20 µM); 1 hour, static incubation. High glucose was significantly different than low glucose (1.7 mM) for all conditions (p<0.03). PGE1 and L-798,106 significantly altered insulin secretion from islets obtained from diabetic mice, but not islets obtained from non-diabetic mice. The data are representative of three independent experiments.

Ptger3 Antagonist Normalizes Insulin Secretion from Islets Obtained from Diabetic Mice As a first step in testing their hypothesis that the EP3 signaling pathway contributes to the pathophysiology of T2D, the Inventors subjected islets isolated from 10-week-old BTBR lean and Ob mice to treatment with a selective agonist (PGE1) or specific antagonist (L-798,106) of the EP3 receptor to monitor the impact on GSIS. Briefly, mouse islets were incubated in medium containing 1.7 mM glucose (non-stimulatory towards insulin secretion) or 16.7 mM glucose (stimulatory towards insulin secretion), with and without the addition of 5 µM PGE1 or 20 µM L-798,106. PGE1 had already been shown to effectively blunt GSIS through G-alpha-i proteins in a beta cell line (Kimple et al. (2005)), and to be relatively selective for EP3 (Kiriyama et al., *Br. J. of Pharmacology* 122: 217-224 (1997)); thus, the Inventors chose PGE1 as the EP3 agonist in this initial experiment. The results show that PGE1 reduced GSIS from islets obtained from diabetic BTBR mice, but had no effect on islets obtained from non-diabetic mice (FIG. 5). Similarly, the EP3-specific small molecule antagonist L-798,106 (Tocris) enhanced GSIS from islets obtained from diabetic mice, restoring GSIS to that observed in islets obtained from non-diabetic mice, yet had no effect on GSIS from islets obtained from non-diabetic mice. These results indicate: (1) the EP3 signaling pathway results in a blockade of GSIS and is functionally upregulated in diabetic BTBR mice, and (2) that an endogenous agonist for EP3 is being synthesized by the diabetic islets themselves, as the antagonist would have no effect if there were no agonist with which to compete for receptor binding.

qRT-PCR analysis of PGE2 synthetic pathway components revealed that two prostaglandin-endoperoxidase synthases (Ptgs1 and Ptgs2, also referred to as COX-1 and COX-2) are up-regulated in islets from diabetic BTBR mice relative to islets from lean BTBR mice (FIG. 3). This finding is consistent with the increased expression of PGE2 synthetic enzymes observed in mouse and human subjects with T2D.

Taken together, the Inventors' functional and expression analyses indicate that both the endogenous ligand for the EP3 receptor (PGE2) and expression of the receptor itself are up-regulated specifically in diabetic mice relative to lean mice, suggesting a possible mechanism for islet dysfunction in T2D.

Example 5

EP3 Antagonist Enhances Insulin Secretion from Human Islets Obtained from Diabetic Subjects To determine if the EP3 signaling pathway regulates insulin secretion in diabetic humans, islets were obtained from cadaveric donors that were either non-diabetic (n=7) or confirmed T2D patients (n=4). The average age of human donors was ~52 years and was not significantly different between non-diabetics and diabetics. The average BMI was significantly different (p<0.04) between diabetics (BMI=41) and non-diabetics (BMI=30), although both groups would be classified as obese.

Figure 6:
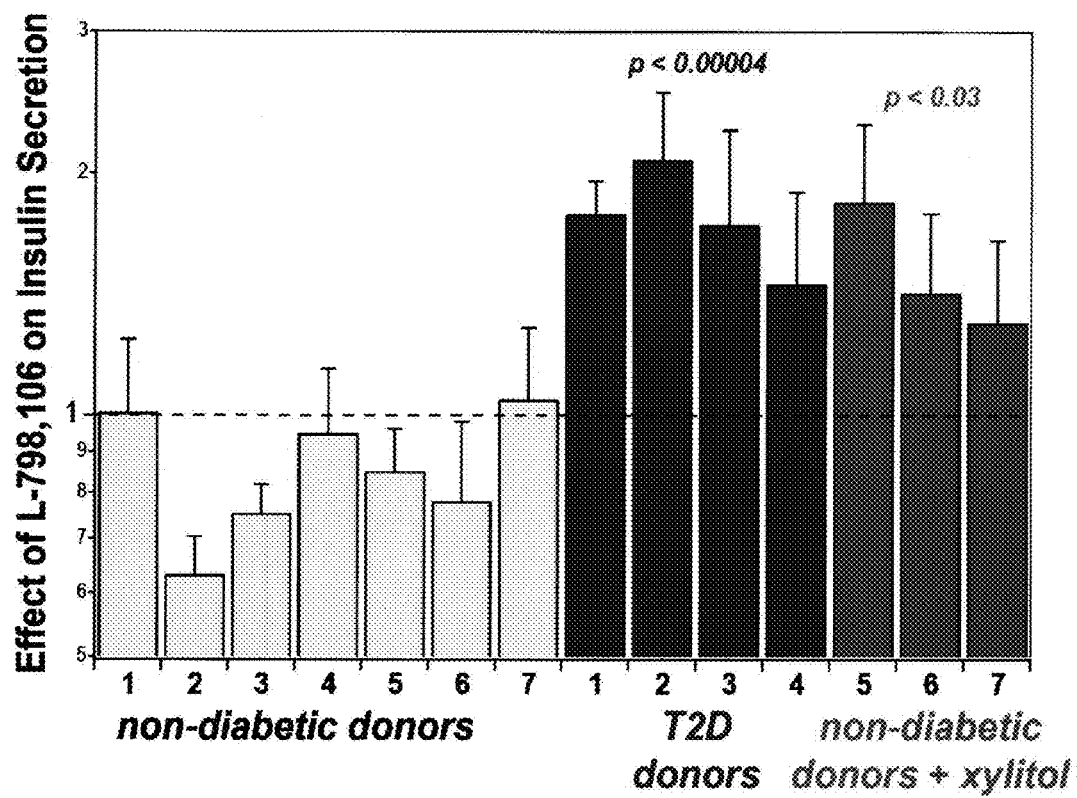
FIG. 6 illustrates that a Ptger3 antagonist can enhance insulin secretion from diabetic human islets. Insulin secretion assays were performed with islets obtained from human cadaveric organ donors that were either non-diabetic or from patients confirmed to have T2D. High glucose (16.7 mM) was used to stimulate insulin secretion in the absence or presence of the L-798,106 (20 µM) in a 45 minute static incubation. Data are represented as the fold potentiation of insulin secretion relative to high-glucose alone. Means and error bars represent the experimental mean+/−SEM for each human islet sample. Islets obtained from non-diabetic donors 5-7, which were non-responsive to L-798-106, were incubated overnight in low glucose medium (8 mM) containing 0.5 mM xylitol to mimic high glucose exposure without the confounding effects of chronic insulin secretion. Under these conditions, L-798,106 was effective to promote glucose dependent insulin secretion.
Figure 7:
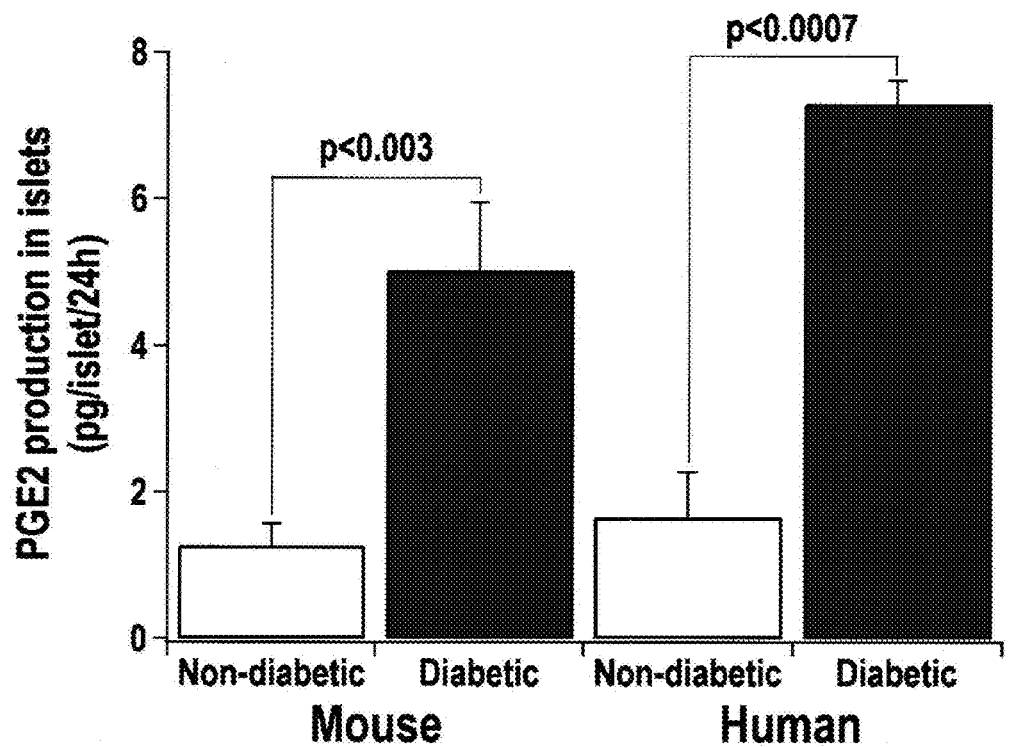
FIG. 7 illustrates that PGE2 production is elevated in islets from diabetic mice or diabetic humans. Islets were cultured for 24 hours in medium containing 8 mM glucose. The amount of PGE2 secreted into the medium was determined by a specific assay and was normalized to the total number of islets used for each measurement.

Non-diabetic and T2D human islets were cultured for 48 hours in 8 mM glucose. A subset of the non-diabetic donor islets were also incubated with 0.5 mM xylitol, a glucose analog that is non-metabolizable beyond glucose-6 phosphate, during the final 24 hour culture period. This concentration of xylitol in combination with sub-stimulatory glucose has been shown to increase expression of genes that are regulated by ChREBP. Xylitol activates the FoxO1 transcription factor via glucose-6 phosphate formation, providing an alternative mechanism for up-regulating gene expression. Following 48 hours in culture, cellular insulin secretion was stimulated for 45 minutes with 16.7 mM glucose in the absence and presence of 10 µM L-798,106. Secreted insulin was normalized to total insulin content in order to determine the fractional release of insulin. Data from each human islet set was normalized to its own response in 16.7 mM glucose alone to isolate the effect of L-798,106 on GSIS (FIG. 6). Responses of T2D donor islets and xylitol-incubated non-diabetic donor islets to L-798,106 both differed significantly from responses of non-diabetic islets incubated in 8 mM glucose alone. Measurement of PGE2 production by non-diabetic and confirmed T2D human islets revealed significant increase in PGE2 production by T2D islets relative to non-diabetic islets (FIG. 7). These data suggest that (1) hyperglycemia up-regulates one or more of the components of the EP3 signaling pathway in human islets, similar to diabetic mouse islets, and (2) that this up-regulation can be mimicked by stimulation of glucose-responsive transcriptional activators.

Taken together, the Inventors' results from non-diabetic and diabetic mouse and human islets suggest that: (1) EP3 expression and activity are induced in parallel with diabetes in both mouse and human islets, and (2) as a cell-surface receptor, EP3 is a potentially druggable target for anti-diabetic therapeutics.

Example 6

EP3 Antagonist Enhances Insulin Secretion from a Rat-Derived Insulinoma Cell Line Rat Ins-1 beta cell lines stably expressing the human pro-insulin gene are used as a models of physiological insulin secretion in response to glucose. The rat Ins-1 beta cell line Ins-1 832/3 responds strongly to both glucose and cyclic AMP (cAMP) potentiation of GSIS and demonstrates high EP3 expression relative to the other E prostanoid receptor isoforms (e.g., EP1, EP2, and EP4) (data not shown). Thus, Ins-1 832/3 is a suitable model for elucidating EP3 agonist/antagonist binding kinetics on the GSIS response.

Figure 8:
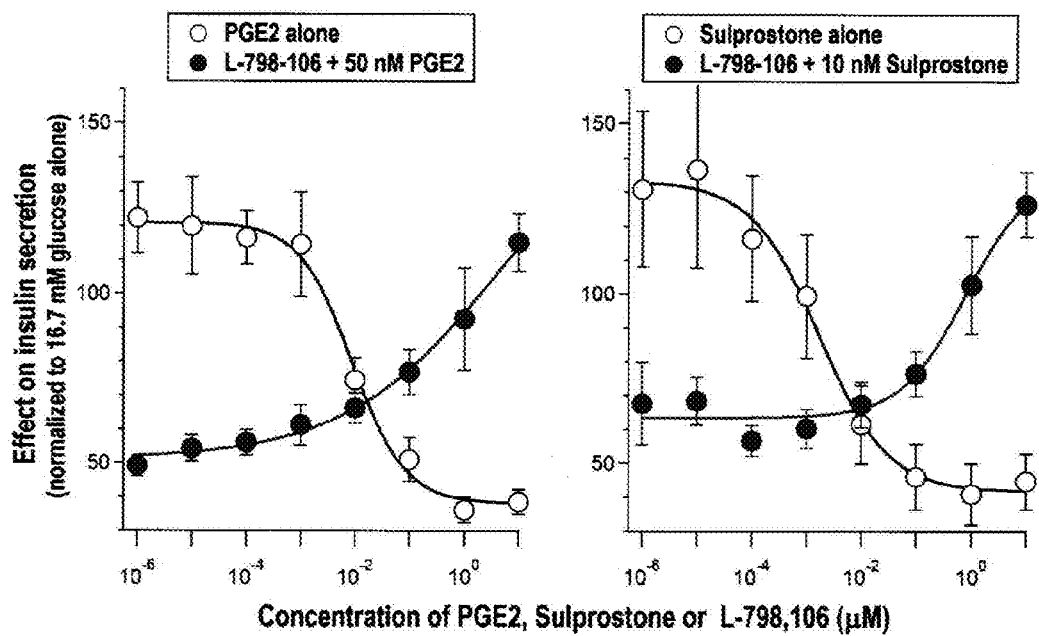
FIG. 8 illustrates that both the natural ligand of EP3 (PGE2) and a specific agonist (sulprostone) dose-dependently suppresses insulin secretion from beta cells. The EP3 antagonist L-798,106 suppresses the effects of PGE2, restoring insulin secretion to levels observed in the absence of the EP3 agonists. Insulin secretion was monitored from the rat insulinoma beta cell line Ins-1 832/3 in response to high glucose (16.7 mM). Increasing concentrations of PGE2 resulted in ~80% maximal reduction in insulin secretion, indicating functional Ptger3 receptor expression. Parallel studies show a high level of Ptger3 expression in Ins-1 cells. The approximate IC50 for PGE2 was ~10 nM. In the presence of 50 nM PGE2, increasing concentrations of L-798,106 restored maximal insulin secretion, demonstrating effective inhibition of Ptger3. The approximate EC50 for L-798,106 in the presence of 50 nM (maximal inhibitory concentration) was 100 nM. Similar results were observed for suprostone-mediated suppression of insulin secretion and the reversal of this suppression by L-798,106. All studies were 2 hour static incubations. Data are the mean of at least three independent studies.

Insulin secretion assays in Ins-1 832/3 cells were performed wherein the dose of PGE2 (a physiological agonist of EP3) or sulprostone (an EP3-selective agonist) were varied over a wide concentration range. Both PGE2 and sulprostone dose-dependently inhibited GSIS. The minimum dose of sulprostone yielding maximum effect on GSIS inhibition was approximately 10 nM and the minimum dose of PGE2 was approximately 50 nM. Dose response analysis of L-798,106 in medium containing stimulatory glucose and 10 nM sulprostone or medium containing 50 nM PGE2 revealed that both PGE2- and sulprostone-dependent suppression of GSIS in Ins-1 cells was reversed in a dose-dependent manner (FIG. 8). These results suggest that the combination of elevated EP3 expression and endogenous E-prostanoid production are required to yield maximal responsiveness to the antagonist, L-798,106.

Example 7

Synergy of GLP-1 and L-798,106 in Improving Diabetic Islet Function

Figure 9:
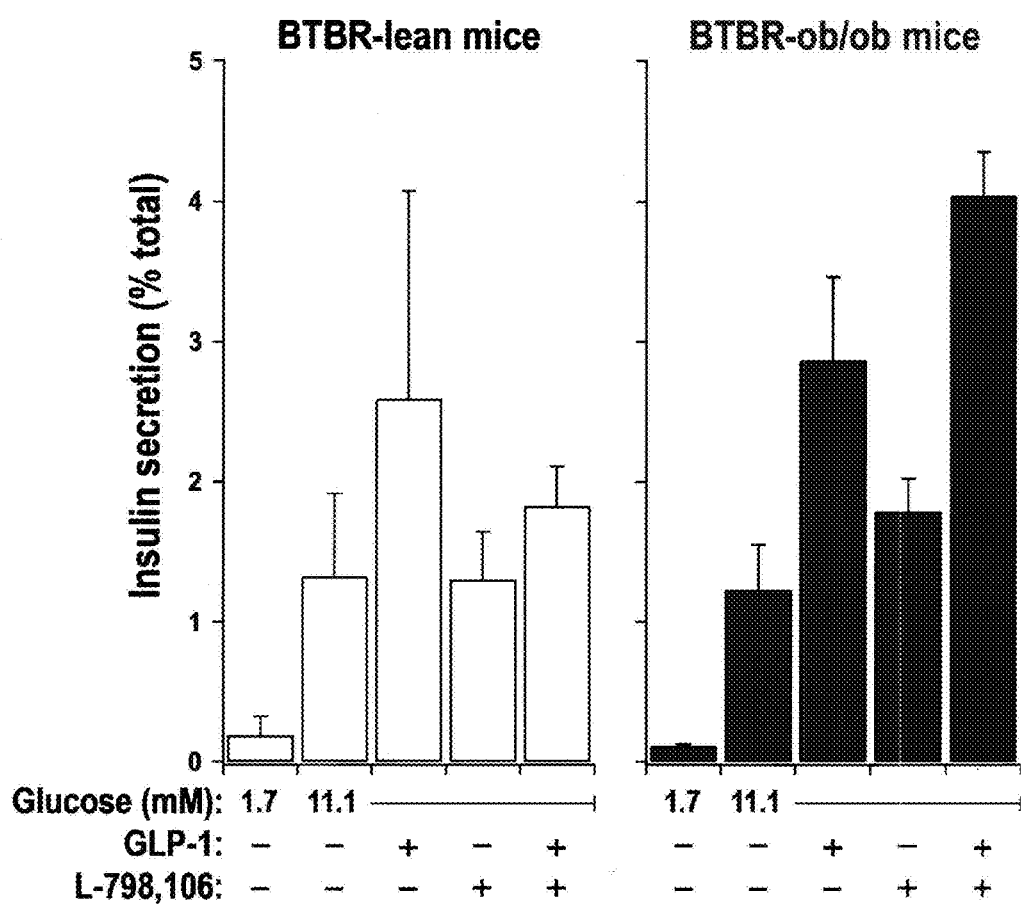
FIG. 9 illustrates that a Ptger3 antagonist can augment the effect of GLP-1 on insulin secretion from islets obtained from diabetic mice. Insulin secretion was measured from islets obtained from non-diabetic BTBR mice (left panel) and from diabetic BTBR-ob/ob mice (right panel) in response to intermediate glucose (11.1 mM) alone, or in the presence of GLP-1 (50 nM) (+,−), L-798,106 (10 µM) (−,+), or the combination of GLP-1 and L-798,106 (+,+). The Ptger3 antagonist augments GLP-1 dependent insulin secretion from diabetic, but not non-islets, demonstrating a synergism between EP3 antagonism and GLP-1 mediated insulin secretion exclusively from diabetic islets.

GLP-1-based therapies are used in T2D therapy. To test the possibility that EP3 antagonism can augment the effect of GLP-1 agonism, islets from diabetic BTBR mice were treated with stimulatory glucose, with and without the addition of 50 nM GLP-1 and/or 10 µM L-198,106, and the level of insulin secretion monitored (FIG. 9). GLP-1 treatment alone had a significant impact on insulin secretion. However, the combination of GLP-1 and L-798,106 had a stronger positive effect on insulin secretion than GLP-1 alone.

Example 8

Figure 10:
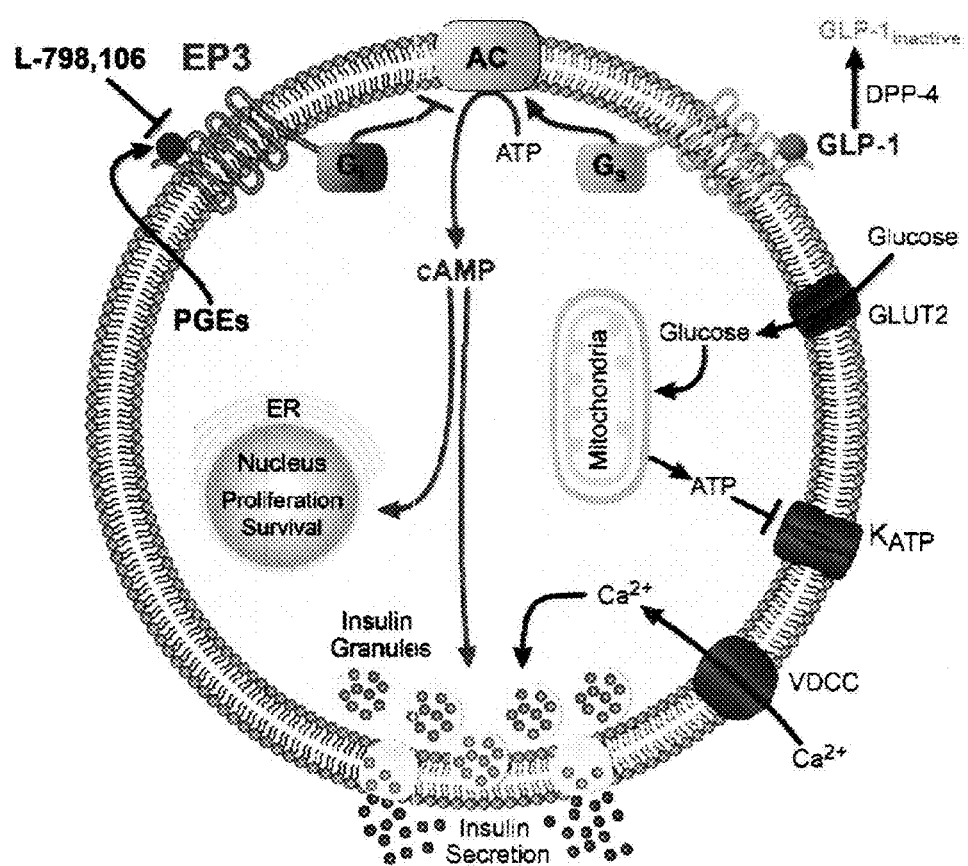
FIG. 10 illustrates the model of inverse regulation of the cAMP signaling pathway in beta cells by EP3 (Ptger3 gene product) and GLP-1. GLP-1 analogs and inhibitors of the DPP-4 enzyme that degrades endogenous GLP-1 all function in the beta cell by increasing cAMP production mediated by AC. cAMP can positively impact both insulin secretion and, potentially, beta cell mass, by activating beta cell proliferation, growth, and survival pathways. The EP3 isoform of the E prostanoid receptor (Ptger3) blocks cAMP production via a Gi-coupled pathway; thus, activated EP3 may oppose all of the functions of GLP-1-based therapeutics in beta cells. Antagonizing the Ptger3 pathway may prove to be a superior therapeutic for T2D, alone or in combination with GLP-1 receptor agonism.

Predicted Role of Ptger3 in Insulin Secretion from Islets Obtained from Diabetic Subjects GLP-1 analogs and inhibitors of the enzyme that degrades endogenous GLP-1 and DPP-4 all function in the beta cell by increasing cyclic AMP (cAMP) production mediated by adenylate cyclase (AC). cAMP can positively impact both insulin secretion and, potentially, beta cell mass, by activating beta cell proliferation, growth, and survival pathways. E prostanoid signaling in the Ins-1 832/13 beta cell line is known to proceed through a member of the G alpha-i subfamily to block GSIS. Activation of EP3 through G alpha-i subfamily members would predictably lead to decreased cAMP production. Thus, the Inventors hypothesized that activated EP3 might oppose all of the functions of GLP-1-based therapeutics in beta cells (FIG. 10). The Inventors predicted that antagonizing the EP3 pathway, alone or in combination with GLP-1 receptor agonism, might prove to be a superior therapeutic for T2D relative to known therapeutics, especially those that target GLP-1.

Sitagliptin, a T2D therapeutic, is a DPP-4 inhibitor that stimulates beta cell cAMP production. However, sitagliptin is ineffective for preventing or treating diabetes in a subset of treated individuals (Raz et al., supra; Aschner et al., supra; Nonaka et al., supra).

The Inventors predict that sitagliptin cannot treat or prevent T2D in individuals in whom Ptger3 expression is at such a level that Ptger3-mediated suppression of adenylate cyclase inhibits cAMP production, thereby preventing insulin secretion from proceeding at physiologically-appropriate levels (FIG. 10).

The Inventors predict that other peptide hormones and small molecules that bind to and activate receptors in the same family as GLP-1 receptor, Subfamily B1, of the secretin receptor family, would also synergize with EP3 antagonists to promote beta cell function if those receptors were expressed on the beta cell. These hormones include other known potentiators of glucose-stimulated insulin secretion (i.e., incretins), including glucose-dependent insulinotropic peptide (or gastric inhibitory peptide (GIP)), Pituitary adenylate cyclase-activating polypeptide (PACAP), and vasoactive intestinal peptide (VIP). Furthermore, agents that act through an alternative stimulatory pathway, such as cholecystokinin (CCK), which on the beta cell binds to a G alpha-q-coupled receptor, might also synergize with Ptger3 antagonists and incretins.

Example 9

Treating Type I Diabetes with a Composition Comprising a Compound that Leads to Activation of Adenylate Cyclase and a Compound that Modulates EP3

Figure 11:
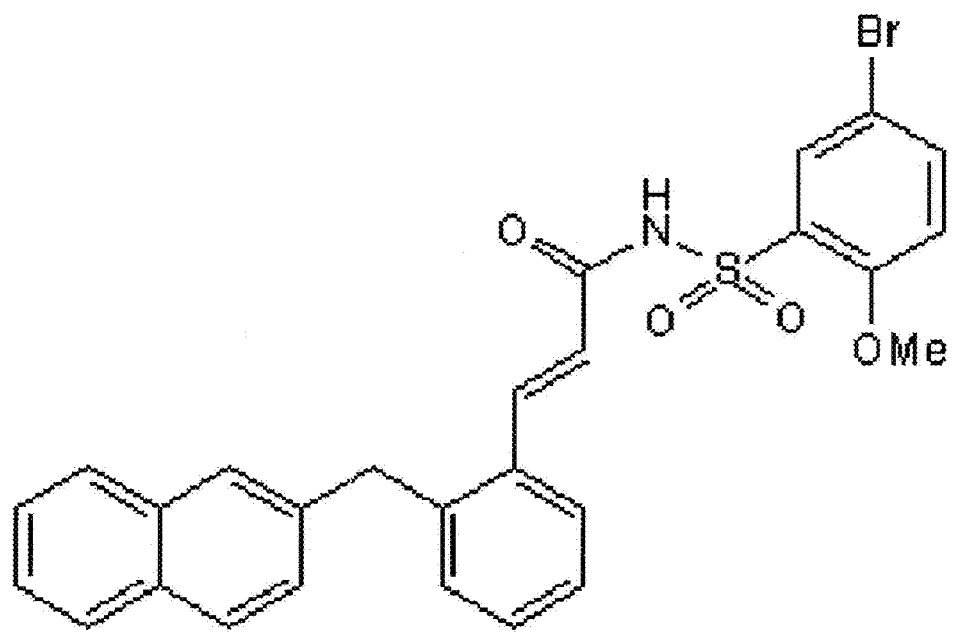
FIG. 11 illustrates the molecular structure of L-798,106; chemical name: (2E)-N-[(5-bromo-2-methoxyphenyl)sulfonyl]-3-[2-(2-naphthalenylmethyl)phenyl]-2-propenamide.
Figure 12:
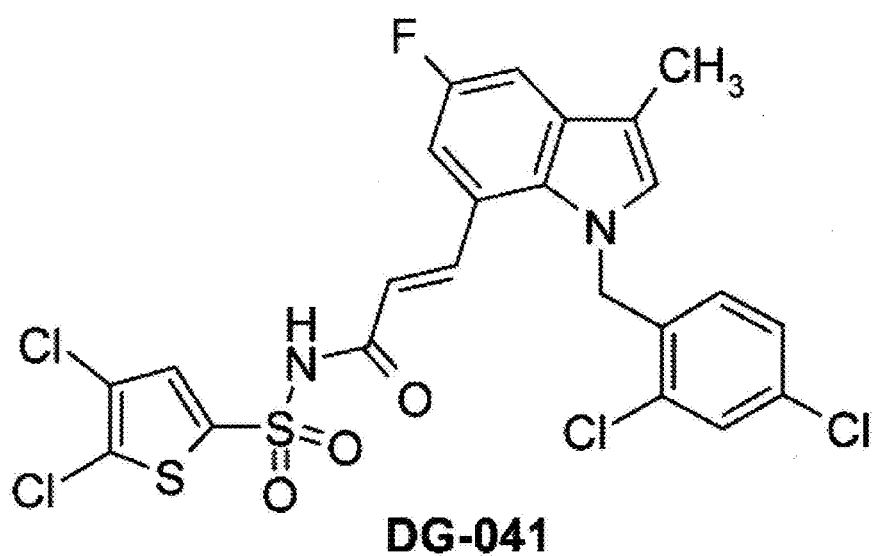
FIG. 12 illustrates the molecular structure of DG-041; chemical name: (2E)-3-[1-[(2,4-dichlorophenyl)methyl]-5-fluoro-3-methyl-1H-indol-7-yl]-N-[(4,5-dichloro-2-thienyl)sulfonyl]-2-propenamide (DG-041).

It is contemplated that a composition comprising a compound that directly or indirectly activates adenylate cyclase (e.g., a compound that activates a GLP-1 receptor, GIP receptor, or PACAP receptor) and a compound that modulates EP3 (e.g., L-798,106; DG-041, or another EP3 antagonist) could be useful for preventing or treating Type I Diabetes (T1D). The molecular structures of L-798,06 and DG-041 are presented in FIG. 11 and FIG. 12, respectively. The composition can comprise any pairwise combination of a compound that directly or indirectly activates adenylate cyclase and a compound that attenuates GSIS-mediated adenylate cyclase inhibition described herein.

Type I Diabetes occurs when immune-mediated pancreatic beta cell destruction leads to near-absolute endogenous insulin deficiency (Mathis et al., *Nature* 414:792-798 (2001); Devendra et al., *BMJ* 328:750-754 (2004)). The residual beta cell function observed in early T1D indicates the presence of a pool of potentially expandable beta cells. A recent strategy for T1D therapy comes from the obesity- and insulin-resistance-linked T2D field. In both T1DM and late-stage T2DM, beta cells fail to maintain sufficient mass and function to properly regulate blood glucose levels (Cnop et al., *Diabetes* 54 Suppl. 2:S97-107 (2005)). Beta cell dysfunction is at least as important as insulin resistance in the pathogenesis of T2DM, if not more so. Thus, nearly all of the newer T2DM treatments in the clinic or under development target beta cell dysfunction and not insulin sensitivity.

As discussed above, agents that stimulate beta cell cAMP production, including DPP-4 inhibitors and GLP-1 analogs, can positively impact beta cell replication, neogenesis and/or survival in rodent models. GLP-1 receptor agonism positively impacts replication and neogenesis in human islets, and GLP-1 treatment can protect both rodent and human beta cells from immune-mediated destruction (Sano et al., supra; Pugazhenthi et al., supra). Testing of GLP-1 agonists and DPP-4 inhibitors in rodent models of T1D and in human T1D patients and pancreatic islet transplant recipients show prolonged survival, improved glycemia, and maintenance of graft function for a longer duration ((Yanay et al., *J. Gene Med.* 12:538-544 (2010)); Kielgast et al., *Curr. Diabetes Rev.* 5:266-275 (2009); Faradji et al., *Cell Transplant* 18:1247-1259 (2009)).

These studies suggest that T1D could be prevented or treated with therapeutics that act through cAMP production, including the compositions and methods of the present invention.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

We claim:

1. A method for increasing insulin secretion from beta cells of a diabetic individual, the method comprising administering to the individual a therapeutic combination comprising therapeutically effective amounts of (1) a compound that directly or indirectly activates adenylate cyclase and (2) an E prostanoid 3 receptor antagonist that attenuates G alpha-i-subfamily-mediated adenylate cyclase inhibition, whereby the beta cells secrete more insulin after the therapeutic combination is administered than before, and wherein the amount of insulin secreted by the beta cells is increased relative to that secreted by beta cells of a diabetic individual not receiving the combination or receiving either the adenylate cyclase-activating compound or the E prostanoid 3 receptor antagonist alone, wherein the diabetic individual is an individual who fails to achieve a glycosylated hemoglobin target of less than 7% after receiving the agent that activates adenylate cyclase without receiving the E prostanoid 3 receptor antagonist.

2. The method of claim 1, wherein the compound that directly or indirectly activates adenylate cyclase is selected from the group consisting of a compound that activates a glucagon-like peptide-1 (GLP-1) receptor, a compound that activates a gastric inhibitory peptide (GIP) receptor, and a compound that activates a pituitary adenylate cyclase-activating peptide (PACAP) receptor.

3. The method of claim 2, wherein the compound that activates the GLP-1 receptor is selected from the group consisting of a DPP-4 inhibitor and an incretin mimetic.

4. The method of claim 1, wherein the E prostanoid 3 receptor antagonist is L-798,106.

5. The method of claim 1, wherein the compound that directly or indirectly activates adenylate cyclase is sitagliptin and the E prostanoid 3 receptor antagonist is L-98,106.

6. The method of claim 1, wherein the E prostanoid 3 receptor antagonist is DG-041.

7. The method of claim 1, wherein the compound that directly or indirectly activates adenylate cyclase is sitagliptin and the E prostanoid 3 receptor antagonist is DG-041.

8. A method of treating diabetes in an individual, the method comprising administering to a diabetic individual in need of increased insulin secretion a therapeutic combination comprising therapeutically effective amounts of (1) a compound that directly or indirectly activates adenylate cyclase and (2) an E prostanoid 3 receptor antagonist that attenuates G alpha-i-subfamily-mediated adenylate cyclase inhibition, whereby beta cells of the individual secrete more insulin after the therapeutic combination is administered than before, wherein insulin secretion is increased relative to that of beta cells of a diabetic individual not receiving the combination or receiving either the adenylate cyclase-activating compound or the E prostanoid 3 receptor antagonist alone, and whereby the increased insulin secretion treats diabetes in the individual, wherein the diabetic individual is an individual who fails to achieve a glycosylated hemoglobin target of less than 7% after receiving the agent that activates adenylate cyclase without receiving the E prostanoid 3 receptor antagonist.

9. The method of claim 8, wherein the compound that directly or indirectly activates adenylate cyclase is selected from the group consisting of a compound that activates a GLP-1 receptor, a compound that activates a GIP receptor, and a compound that activates a PACAP receptor.

10. The method of claim 9, wherein the compound that activates the GLP-1 receptor is selected from the group consisting of a DPP-4 inhibitor and an incretin mimetic.

11. The method of claim 8, wherein the E prostanoid 3 receptor antagonist is L-798,106.

12. The method of claim 8, wherein the compound that directly or indirectly activates adenylate cyclase is sitagliptin and the E prostanoid 3 receptor antagonist is L-798,106.

13. The method of claim 8, wherein the E prostanoid 3 receptor antagonist is DG-041.

14. The method of claim 8, wherein the compound that directly or indirectly activates adenylate cyclase is sitagliptin and the E prostanoid 3 receptor antagonist is DG-041.

15. The method of claim 8, wherein the diabetes is Type II diabetes.

16. The method of claim 8, wherein the therapeutic combination comprises more than one compound that directly or indirectly activates adenylate cyclase.

17. The method of claim 8, wherein the therapeutic combination comprises more than one E prostanoid 3 receptor antagonist that attenuates G alpha-i-subfamily-mediated adenylate cyclase inhibition.

18. The method of claim 1, wherein the compound that directly or indirectly activates adenylate cyclase is a GLP-1 mimetic or a DPP-4 inhibitor.

19. The method of claim 1, wherein the therapeutically effective amounts are lower than effective amounts of the adenylate cyclase-activating compound or the E prostanoid 3 receptor antagonist when either is administered alone.

* * * * *